United States Patent
He et al.

(10) Patent No.: US 11,998,308 B2
(45) Date of Patent: Jun. 4, 2024

(54) METHOD AND APPARATUS FOR DETERMINING RESPIRATION PHASE, MAGNETIC RESONANCE IMAGING METHOD AND SYSTEM

(71) Applicant: Siemens Healthcare GmbH, Erlangen (DE)

(72) Inventors: Jin Qiang He, Shenzhen (CN); De He Weng, Shenzhen (CN); Shu Qun Xie, Shenzhen (CN); Fang Dong, Shenzhen (CN)

(73) Assignee: Siemens Healthineers AG, Erlangen (DE)

( * ) Notice: Subject to any disclaimer, the term of this patent is extended or adjusted under 35 U.S.C. 154(b) by 770 days.

(21) Appl. No.: 16/998,340

(22) Filed: Aug. 20, 2020

(65) Prior Publication Data
US 2021/0052187 A1 Feb. 25, 2021

(30) Foreign Application Priority Data
Aug. 21, 2019 (CN) .......................... 201910772771.5

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0816* (2013.01); *A61B 5/113* (2013.01); *A61B 5/7235* (2013.01);
(Continued)

(58) Field of Classification Search
CPC ..... A61B 5/055; A61B 5/7264; A61B 5/7267; A61B 5/7285; A61B 5/7289; A61B 5/7292
See application file for complete search history.

(56) References Cited

U.S. PATENT DOCUMENTS

| 11,266,838 B1 * | 3/2022 | Tehrani .............. A61N 1/36139 |
| 2005/0197586 A1 * | 9/2005 | Pearlman ............. A61B 5/7267 |
| | | 600/509 |

(Continued)

FOREIGN PATENT DOCUMENTS

| CN | 108634974 A | * | 10/2018 | ............. A61B 5/113 |
| WO | WO-2018060502 A1 | * | 4/2018 | |
| WO | WO-2020240464 A1 | * | 12/2020 | |

OTHER PUBLICATIONS

Bailón, R., Laouini, G., Grao, C., Orini, M., Laguna, P., & Meste, O. (2010). The integral pulse frequency modulation model with time-varying threshold: application to heart rate variability analysis during exercise stress testing. IEEE transactions on biomedical engineering, 58(3), 642-652. (Year: 2010).*

(Continued)

*Primary Examiner* — Keith M Raymond
*Assistant Examiner* — Johnathan Maynard
(74) *Attorney, Agent, or Firm* — Banner & Witcoff Ltd.

(57) ABSTRACT

The present disclosure provides techniques for determining a respiration phase by extracting a distance characteristic value, a score characteristic value, and an area characteristic value from the respiration signal, wherein the distance characteristic value, the score characteristic value and the area characteristic value are used to indicate waveform variation between two adjacent waveforms in the respiration signal. The techniques include training a respiration signal model according to the distance characteristic value, the score characteristic value, and the area characteristic value to determine the respiration phase of the respiration signal using the respiration signal model.

19 Claims, 5 Drawing Sheets

(51) Int. Cl.
*A61B 5/08* (2006.01)
*A61B 5/113* (2006.01)
(52) U.S. Cl.
CPC .......... *A61B 5/7264* (2013.01); *A61B 5/7267* (2013.01); *A61B 5/7271* (2013.01); *A61B 5/7275* (2013.01); *A61B 5/7292* (2013.01); *A61B 5/7285* (2013.01)

(56) References Cited

U.S. PATENT DOCUMENTS

| | | | |
|---|---|---|---|
| 2011/0004081 A1* | 1/2011 | Addison | A61B 5/08 600/538 |
| 2012/0179061 A1* | 7/2012 | Ramanan | A61B 5/087 128/204.23 |
| 2013/0080489 A1* | 3/2013 | Ochs | A61B 5/02416 708/201 |
| 2016/0371833 A1* | 12/2016 | Prasad | A61B 5/1128 |
| 2017/0071553 A1* | 3/2017 | Hwang | A61B 5/7285 |
| 2017/0209074 A1* | 7/2017 | Siu | A61B 5/0873 |
| 2018/0070859 A1* | 3/2018 | Colman | A61B 5/746 |
| 2018/0106897 A1* | 4/2018 | Shouldice | A61B 5/0507 |
| 2019/0029531 A1* | 1/2019 | Doukky | A61B 5/7235 |
| 2019/0110702 A1* | 4/2019 | Thaveeprungsriporn | A61B 5/02108 |
| 2020/0253547 A1* | 8/2020 | Harris | A61B 5/0022 |
| 2021/0154421 A1* | 5/2021 | Xu | A61M 16/0003 |
| 2021/0364589 A1* | 11/2021 | Bilgic | A61B 5/7207 |
| 2022/0305227 A1* | 9/2022 | Rüller | G16H 40/63 |

OTHER PUBLICATIONS

Lázaro, J., Gil, E., Bailón, R., Mincholé, A., & Laguna, P. (2013). Deriving respiration from photoplethysmographic pulse width. Medical & biological engineering & computing, 51, 233-242. (Year: 2013).*

Lázaro, J., Nam, Y., Gil, E., Laguna, P., & Chon, K. H. (May 2014). Smartphone-camera-acquired pulse photoplethysmographic signal for deriving respiratory rate. In 2014 8th Conference of the European Study Group on Cardiovascular Oscillations (ESGCO) (pp. 121-122). IEEE. (Year: 2014).*

Lázaro, J., Nam, Y., Gil, E., Laguna, P., & Chon, K. H. (2015). Respiratory rate derived from smartphone-camera-acquired pulse photoplethysmographic signals. Physiological measurement, 36(11), 2317. (Year: 2015).*

J. Gordon Betts, Kelly A. Young, James A. Wise, Eddie Johnson, Brandon Poe, Dean H. Kruse, Oksana Korol, Jody E. Johnson, Mark Womble, Peter DeSaix., "Anatomy and Physiology: 22.3 The Process of Breathing." 2013, OpenStax (Year: 2013).*

* cited by examiner

METHOD AND APPARATUS FOR DETERMINING RESPIRATION PHASE, MAGNETIC RESONANCE IMAGING METHOD AND SYSTEM

CROSS-REFERENCE TO RELATED APPLICATIONS

The present application claims the benefit of the filing date of China patent application no. CN 201910772771.5, filed on Aug. 21, 2019, the contents of which are incorporated herein by reference in their entirety.

TECHNICAL FIELD

The present disclosure relates to the field of medical magnetic resonance imaging (MRI) and, in particular, to techniques for determining a respiration phase for use in MRI systems.

BACKGROUND

MRI is a type of tomography, which exploits the phenomenon of magnetic resonance to obtain electromagnetic signals from an examination subject such as a human body, and reconstructs information. Specifically, an MRI system applies a radio frequency (RF) pulse of a specific frequency to a human body in a static magnetic field, thereby exciting hydrogen protons in the human body so that they experience magnetic resonance. After the pulse stops, the protons generate magnetic resonance (MR) signals in the course of relaxation. Human body information is reconstructed by processing procedures including the reception of MR signals, spatial encoding, and image reconstruction.

During MRI, respiratory motion of the examination subject reduces the MR image quality in regions of the examination subject that are affected by the respiratory motion, such as the abdomen. In order to eliminate motion artefacts in MR images caused by respiratory motion, a respiration sensor is generally used to detect a respiratory motion state of the examination subject and to trigger the acquisition of MR data at an appropriate time.

However, different coil units in the MRI system will receive inconsistent respiratory motion signals; this results in each receiving channel obtaining different respiratory motion information, and these items of information will give rise to differences for different positions of different examination subjects.

SUMMARY

According to one aspect of the embodiments of the present disclosure, a method for determining a respiration phase of a respiration signal is provided. The method comprises: extracting a distance characteristic value, a score characteristic value, and an area characteristic value from the respiration signal, wherein the distance characteristic value, the score characteristic value and the area characteristic value are used to indicate waveform variation between two adjacent waveforms in the respiration signal; training a respiration signal model according to the distance characteristic value, the score characteristic value, and the area characteristic value to determine the respiration phase of the respiration signal using the respiration signal model.

The method described above solves the problem in the related art of being unable to accurately determine a respiration phase of a respiration signal, and has the beneficial effect of being able to accurately determine a respiration phase.

In an exemplary embodiment of the present disclosure, the distance characteristic value is the ratio of the width of a second-half-waveform of a first waveform of the two adjacent waveforms to the width of a first-half-waveform of a second waveform of the two adjacent waveforms; and/or the score characteristic value is the ratio of the width of a rising waveform portion leading to a crest point of the first waveform of the two adjacent waveforms to the width of a falling waveform portion leading to a trough point of the first waveform; and/or the area characteristic value is the ratio of the area formed by two crest points of the two adjacent waveforms and a trough point between the two waveforms to the area formed by the second waveform.

By extracting characteristics characterizing waveform variation between two adjacent waveforms of the respiration signal, e.g. the distance characteristic value, score characteristic value, and area characteristic value, a respiration phase can be identified using respiration curve characteristics by finding by comparing the differences in aspiration and expiration curve shapes.

In an exemplary embodiment of the present disclosure, before extracting the distance characteristic value, score characteristic value, and area characteristic value from the respiration signal, the method further comprises: acquiring a crest point of a first waveform and a crest point of a second waveform of the two waveforms as a first maximum point and a second maximum point, respectively; acquiring a trough point between the two waveforms as a first minimum point, and acquiring a trough point of the second waveform after the second maximum point as a second minimum point; determining time points corresponding to the first maximum point, the first minimum point, the second maximum point, and the second minimum point, respectively, as a first maximum time point, a first minimum time point, a second maximum time point, and a second minimum time point.

The method described above enables the acquisition of relevant extremum points, and time points corresponding thereto, of two adjacent waveforms of the respiration signal, and the acquired extremum points and corresponding time points can then be used to quickly calculate respiration characteristic values associated with waveform variation of the respiration signal.

In an exemplary embodiment of the present disclosure, the step of extracting the distance characteristic value from the respiration signal comprises: calculating the ratio of the difference value between the first minimum time point and the first maximum time point to the difference value between the second maximum time point and the first minimum time point; and taking the calculated ratio to be the extracted distance characteristic value.

By calculating the ratio of the bottom width of the second-half-waveform of the first waveform of the two adjacent waveforms to the bottom width of the first-half-waveform of the second waveform, it is possible to find by comparison the variation between the second-half-waveform of the first waveform and the first-half-waveform of the second waveform, and it is thereby possible to extract the distance characteristic value of the respiration signal.

In an exemplary embodiment of the present disclosure, the step of extracting the score characteristic value from the respiration signal comprises: based on a predetermined amplitude ratio parameter and the first maximum point and the first minimum point, determining a start time point of a rising waveform portion leading to the first maximum point of the first waveform, and a start time point of a falling waveform portion leading to the first minimum point of the first waveform, as a first time point and a second time point, respectively, for determining an end-of-expiration start time point of the respiration phase;

calculating the ratio of the difference value between the first maximum time point and the first time point to the difference value between the first minimum time point and the second time point; and taking the calculated ratio to be the extracted score characteristic value.

By calculating the ratio of the time corresponding to a rising waveform portion leading to the crest point in the first waveform to the time corresponding to a falling waveform portion leading to the trough point in the first waveform, it is possible to find by comparison the variation between the waveform close to the crest and the waveform close to the trough of the first waveform, and thereby to extract the score characteristic value of the respiration signal.

In an exemplary embodiment of the present disclosure, the first time point and the second time point are determined according to the following two Equations, respectively:

$$\mathrm{mag}(t\_1)=\mathrm{mag}(t\_\mathrm{max}1)*p+\mathrm{mag}(t\_\mathrm{min}1)*(1-p); \text{ and}$$

$$\mathrm{mag}(t\_2)=\mathrm{mag}(t\_\mathrm{max}1)*(1-p)+\mathrm{mag}(t\_\mathrm{min}1)*p,$$

wherein $t\_1$ is the first time point, $t\_\mathrm{max}1$ is the first maximum time point, p is the amplitude ratio parameter, $t\_\mathrm{min}1$ is the first minimum time point, and mag is an amplitude function.

The Equations above enable precise calculation of the score characteristic value of the respiration signal.

In an exemplary embodiment of the present disclosure, the amplitude ratio parameter p is equal to 80%.

The amplitude ratio parameter value of 80% is an empirical value determined by taking into account other parameters of an MRI system in practice; by setting the amplitude ratio parameter to 80%, the score characteristic value of the respiration signal can be calculated more precisely.

In an exemplary embodiment of the present disclosure, the step of extracting the area characteristic value from the respiration signal comprises: calculating the ratio of a first polygon area determined by the first maximum point, the second maximum point, and the first minimum point to a second polygon area determined by the first minimum point, the second maximum point, and the second minimum point; and taking the calculated ratio to be the extracted area characteristic value.

By calculating the ratio of the area formed by the two crest points of the two adjacent waveforms and the trough point between the two waveforms to the area formed by the two trough points of the two waveforms and the crest point of the second waveform, it is possible to find by comparison the variation between the first waveform and the second waveform, and it is thereby possible to extract the area characteristic value of the respiration signal.

According to another aspect of the embodiments of the present disclosure, an apparatus for determining a respiration phase of a respiration signal is provided, comprising:

an extraction module configured to extract a distance characteristic value, a score characteristic value, and an area characteristic value from the respiration signal, wherein the distance characteristic value, the score characteristic value, and the area characteristic value are used to indicate waveform variation between two adjacent waveforms in the respiration signal; a determining module configured to train a respiration signal model according to the distance characteristic value, the score characteristic value, and the area characteristic value to determine the respiration phase of the respiration signal using the respiration signal model.

The apparatus described above solves the problem in the related art of being unable to accurately determine a respiration phase of a respiration signal, and has the beneficial effect of being able to accurately determine a respiration phase.

In an exemplary embodiment of the present disclosure, the extraction module comprises:

a maximum point acquisition unit configured to acquire a crest point of a first waveform and a crest point of a second waveform of the two waveforms as a first maximum point and a second maximum point respectively; a minimum point acquisition unit configured to acquire a trough point between the two waveforms as a first minimum point, and acquire a trough point of the second waveform after the second maximum point as a second minimum point; and a time point determining unit configured to determine time points corresponding to the first maximum point, the first minimum point, the second maximum point, and the second minimum point, respectively, as a first maximum time point, a first minimum time point, a second maximum time point, and a second minimum time point.

The apparatus described above enables the acquisition of relevant extremum points, and time points corresponding thereto, of two adjacent waveforms of the respiration signal, and the acquired extremum points and corresponding time points can then be used to quickly calculate respiration characteristic values associated with waveform variation of the respiration signal.

In an exemplary embodiment of the present disclosure, the extraction module comprises:

a distance calculating unit configured to calculate the ratio of the difference value between the first minimum time point and the first maximum time point to the difference value between the second maximum time point and the first minimum time point; and a distance extraction unit configured to take the calculated ratio to be the extracted distance characteristic value.

By calculating the ratio of the bottom width of the second-half-waveform of the first waveform of the two adjacent waveforms to the bottom width of the first-half-waveform of the second waveform, it is possible to find by comparison the variation between the second-half-waveform of the first waveform and the first-half-waveform of the second waveform, and it is thereby possible to extract the distance characteristic value of the respiration signal.

In an exemplary embodiment of the present disclosure, the extraction module comprises:

a characteristic point determining unit configured to determine, based on a predetermined amplitude ratio parameter and the first maximum point and the first minimum point, a start time point of a rising waveform portion leading to the first maximum point of the first waveform, and a start time point of a falling waveform portion leading to the first minimum point of the first waveform, as a first time point and a second time point, respectively, for determining an end-of-expiration start time point of the respiration phase; a characteristic point calculating unit configured to calculate the ratio of the difference value between the first maximum time point and the first time point to the difference value between the first minimum time point and the second time point; and a characteristic point extraction unit configured to take the calculated ratio to be the extracted score characteristic value.

By calculating the ratio of the time corresponding to a rising waveform portion leading to the crest point in the first waveform to the time corresponding to a falling waveform portion leading to the trough point in the first waveform, it is possible to find by comparison the variation between the waveform close to the crest and the waveform close to the trough of the first waveform, and thereby possible to extract the score characteristic value of the respiration signal.

In an exemplary embodiment of the present disclosure, the extraction module comprises:

an area calculating unit configured to calculate the ratio of a first polygon area determined by the first maximum point, the second maximum point, and the first minimum point to a second polygon area determined by the first minimum point, the second maximum point, and the second minimum point; and an area characteristic extraction unit configured to take the calculated ratio to be the extracted area characteristic value.

By calculating the ratio of the area formed by the two crest points of the two adjacent waveforms and the trough point between the two waveforms to the area formed by the two trough points of the two waveforms and the crest point of the second waveform, it is possible to find by comparison the variation between the first waveform and the second waveform, and it is thereby possible to extract the area characteristic value of the respiration signal.

According to another aspect of the present disclosure, a magnetic resonance imaging method is provided, comprising:

determining a respiration phase of a respiration signal according to the method provided in the present disclosure for determining a respiration phase of a respiration signal; and performing magnetic resonance imaging of an examination region of an examination subject according to the determined respiration phase.

In the method described above, determining the end-of-expiration phase of the respiration signal makes it possible to trigger an MRI system to perform a scan at the start time point of the end-of-expiration phase determined, thereby avoiding motion artefacts in MRI.

According to another aspect of the present disclosure, an MRI system is provided, comprising:

the apparatus provided in the present disclosure for determining a respiration phase of a respiration signal configured to determine a respiration phase of a respiration signal; and an imaging apparatus configured to perform magnetic resonance imaging of an examination region of an examination subject according to the determined respiration phase.

In the MRI system described above, determining the end-of-expiration phase of the respiration signal makes it possible to trigger an MRI system to perform a scan at the start time point of the end-of-expiration phase determined, thereby avoiding motion artefacts in MRI.

According to another aspect of the present disclosure, a non-transitory readable storage medium having a program stored thereon is provided and, when the program is executed, a processor is caused to execute any of the methods provided in the present disclosure for determining a respiration phase of a respiration signal.

BRIEF DESCRIPTION OF THE DRAWINGS/FIGURES

The drawings described here are used to provide a better understanding of the present disclosure and form part of the present disclosure; the schematic embodiments of the present disclosure and the descriptions thereof are used to explain the present disclosure, but do not constitute an improper limitation of the present disclosure. In the drawings.

DETAILED DESCRIPTION

To enable those skilled in the art to better understand the present disclosure, embodiments of the present disclosure are described clearly and completely below in conjunction with the drawings accompanying the present disclosure; obviously, the embodiments which are described are merely some, and not all, of the embodiments of the present disclosure. All other embodiments obtained by those skilled in the art on the basis of the embodiments in the present disclosure without expending creative effort shall fall within the scope of protection of the present disclosure.

Figure 1:
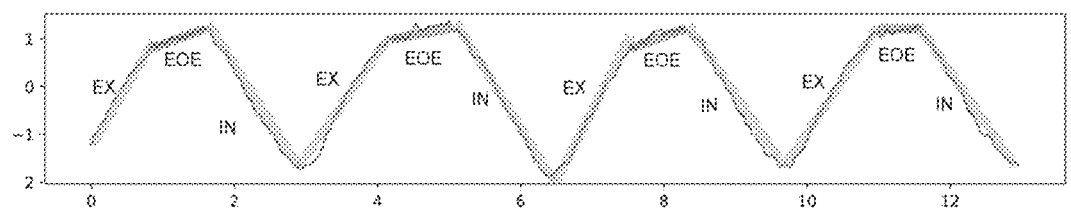
FIG. 1 is a timing diagram of a respiration signal according to the related art.

According to a natural understanding of respiratory motion, in general, a respiratory motion cycle consists of three phases: aspiration, expiration, and end-of-expiration. FIG. 1 is a timing diagram of a respiration signal according to the related art, wherein the horizontal axis represents time and the vertical axis represents the amplitude of respiration. As shown in FIG. 1, EX denotes the expiration phase, IN denotes the aspiration phase, and EOE denotes the end-of-expiration phase. When expiration is about to end, i.e. in the EOE phase, respiratory motion is very small. In the case of MRI, if image data is acquired in the EOE phase, motion artifacts can be ignored. As can be seen, the crux of the problem is thus how to determine the EOE phase of the respiration signal.

Figure 2:
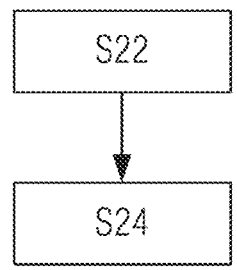
FIG. 2 is a flow chart of the method for determining a respiration phase of a respiration signal, in accordance with an embodiment of the present disclosure.

An exemplary embodiment of the present disclosure provides a method for determining a respiration phase of respiratory motion. FIG. 2 is a flow chart of the method for determining a respiration phase of a respiration signal according to an embodiment of the present disclosure. As shown in FIG. 2, the method comprises the following steps:

Step S22: extracting respiration characteristic values from the respiration signal.

Respiration characteristic values such as a distance characteristic value, a score characteristic value, and an area characteristic value are extracted from the respiration signal. These respiration characteristic values are used to indicate waveform variation between two adjacent waveforms in the respiration signal. Thus, by finding by comparison the waveform variation between two adjacent waveforms, using differences in the shape of aspiration and expiration curves, it is possible to determine an EOE phase in one waveform.

Step S24: training a respiration signal model according to the extracted respiration characteristic values, and using the respiration signal model to determine a respiration phase of the respiration signal.

After these respiration characteristic values have been extracted from the respiration signal, e.g. a Pilot Tone respiration signal, they may be used to train a Support Vector Machine (SVM) model. When the SVM model has been trained, this model can be used to determine a respiration phase of the respiration signal.

Figure 3:
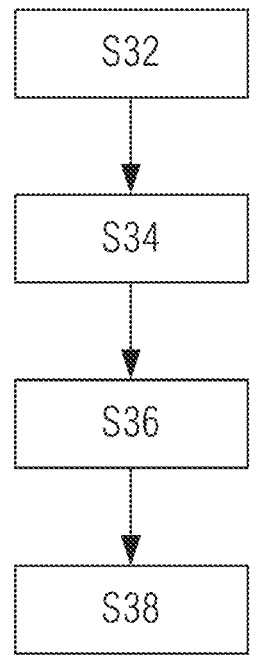
FIG. 3 is a flow chart of the acquisition of respiration characteristic values, in accordance with an embodiment of the present disclosure.

FIG. 3 is a flow chart of the acquisition of respiration characteristic values according to an embodiment of the present disclosure; as shown in FIG. 3, the method comprises the following steps:

Step S32: determining extremum points of two adjacent waveforms of the respiration signal and corresponding time points.

Figure 4:
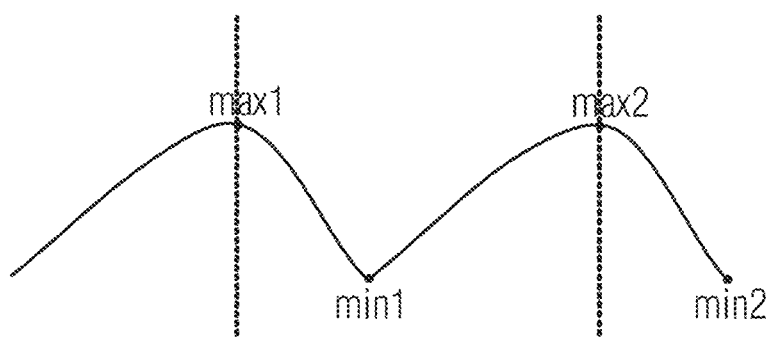
FIG. 4 is a schematic diagram showing two adjacent waveforms of the respiration signal, in accordance with an embodiment of the present disclosure.

FIG. 4 is a schematic diagram showing two adjacent waveforms of the respiration signal according to an embodiment of the present disclosure, wherein the horizontal direction represents time, and the vertical direction represents the amplitude of the respiration signal.

First, a crest point of a first waveform and a crest point of a second waveform of the two waveforms are acquired as a first maximum point max1 and a second maximum point max2, respectively. Next, a trough point between the two waveforms is acquired as a first minimum point min1, and a trough point immediately after the second maximum point max2 is acquired as a second minimum point min2.

Next, time points corresponding to the first maximum point max1, the first minimum point min1, the second maximum point max2, and the second minimum point min2, respectively, are determined, i.e. a first maximum time point t_max1, a first minimum time point t_min1, a second maximum time point t_max2, and a second minimum time point t_min2.

Step S34: determining a distance characteristic value.

After the extremum points and the time points corresponding thereto have been determined, the corresponding time points are used to calculate the distance characteristic value.

Figure 5:
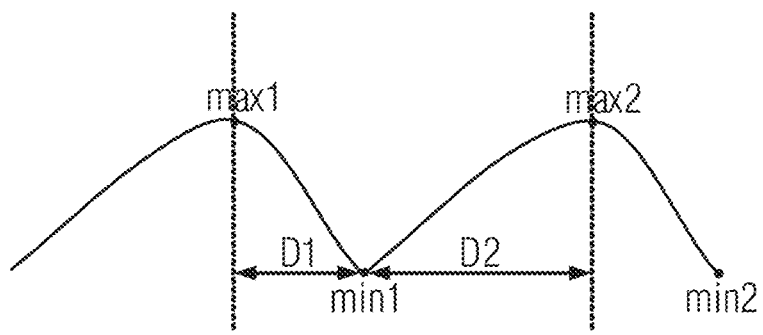
FIG. 5 is a schematic diagram showing distance characteristics of the respiration signal, in accordance with an embodiment of the present disclosure.

FIG. 5 is a schematic diagram showing distance characteristics of the respiration signal according to an embodiment of the present disclosure. As shown in FIG. 5, D1 denotes a distance difference value between the first minimum time point t_min1 and the first maximum time point t_max1, and D2 denotes a distance difference value between the second maximum time point t_max2 and the first minimum time point t_min1. The distance characteristic value can be calculated using the following Equation 1:

$$f1=(t\_min1-t\_max1)/(t\_max2-t\_min1). \quad \text{Eqn. 1:}$$

The formula above may also be expressed as f1=D1/D2, wherein f1 denotes the distance characteristic value.

Step S36: determining a score characteristic value.

After the extremum points and the time points corresponding thereto have been determined, the corresponding time points are used to calculate the score characteristic value.

Figure 6:
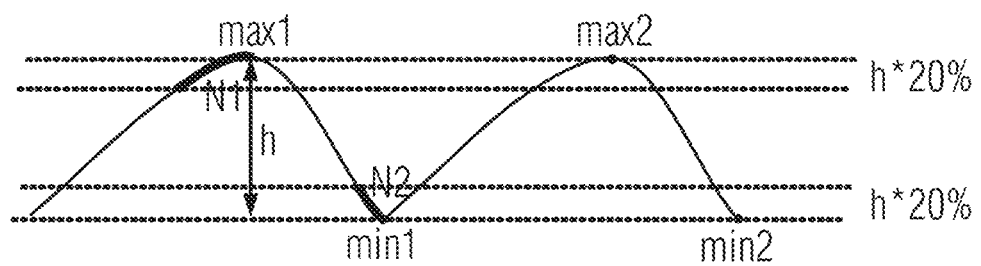
FIG. 6 is a schematic diagram showing score characteristics of the respiration signal, in accordance with an embodiment of the present disclosure.

FIG. 6 is a schematic diagram showing score characteristics of the respiration signal according to an embodiment of the present disclosure. As shown in FIGS. 6, N1 and N2 denote possible EOE phases on the first waveform, and h denotes the amplitude of the respiration signal at the first maximum point.

Based on a predetermined amplitude ratio parameter p, the first maximum point max1, and the first minimum point min1, a start time point t_1 (not shown) of a rising waveform portion N1 leading to the first maximum point max1 on the first waveform is determined, and a start time point t_2 (not shown) of a falling waveform portion N2 leading to the first minimum point min1 on the first waveform is determined. As discussed herein, t_1 is referred to as the first time, and t_2_ is referred to as the second time.

In an exemplary embodiment of the present disclosure, the first time t_1 and the second time t_2 are calculated according to the following two Equations, respectively:

$$\mathrm{mag}(t\_1)=\mathrm{mag}(t\_max1)*p+\mathrm{mag}(t\_min1)*(1-p); \text{ and} \quad \text{Eqn. 2:}$$

$$\mathrm{mag}(t\_2)=\mathrm{mag}(t\_max1)*(1-p)+\mathrm{mag}(t\_min1)*p. \quad \text{Eqn. 3:}$$

wherein mag(t) is the amplitude of the respiration signal as a function of time t, and p is the predetermined amplitude ratio parameter.

For example, supposing that the predetermined amplitude ratio parameter p is 80%, then the first time t_1 and second time t_2 should satisfy:

$$\mathrm{mag}(t\_1)=\mathrm{mag}(t\_max1)*0.8+\mathrm{mag}(t\_min1)*0.2; \text{ and} \quad \text{Eqn. 2:}$$

$$\mathrm{mag}(t\_2)=\mathrm{mag}(t\_max1)*0.2+\mathrm{mag}(t\_min1)*0.8. \quad \text{Eqn. 3:}$$

After the possible EOE phase start time points, i.e. the first time point t_1 and second time point t_2, have been determined, the ratio of the difference value between the first maximum time point t_max1 and first time point t_1 to the difference value between the first minimum time point t_min1 and second time point t_2 is calculated, and the result is taken to be the score characteristic value. The following equation is used to calculate the score characteristic value:

$$f2=(t\_max1-t\_1)/(t\_min1-t\_2). \quad \text{Eqn. 4:}$$

Step S38: determining an area characteristic value.

After the extremum points and the time points corresponding thereto have been determined, the corresponding time points are used to calculate the area characteristic value.

Figure 7:
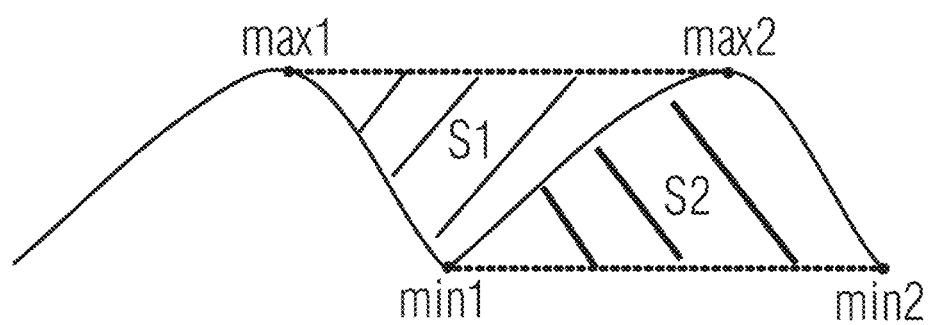
FIG. 7 is a schematic diagram showing area characteristics of the respiration signal, in accordance with an embodiment of the present disclosure.

FIG. 7 is a schematic diagram showing area characteristics of the respiration signal according to an embodiment of the present disclosure. As shown in FIG. 7, the first maximum point max1 and second maximum point max2 are connected, such that a first polygon is formed among the first maximum point max1, the second maximum point max2, and the first minimum point min1, the area thereof being denoted S1. At the same time, the first minimum point min1 and second minimum point min2 are connected, such that a second polygon is formed among the first minimum point min1, the second maximum point max2, and the second minimum point min2, the area thereof being denoted S2.

In an embodiment of the present disclosure, the following equation is used to calculate the area characteristic value:

$$f3=s(t\_max1,t\_max2)/s(t\_min1,t\_min2) \quad \text{Eqn. 5:}$$

f3 denotes the area characteristic value, and s denotes the area of the polygon enclosed by the extremum points; in fact, f3 is the ratio S1/S2 of the two areas S1 and S2 shown in FIG. 7.

The embodiments of the present disclosure do not impose restrictions regarding the order of steps S34-S38 above, which may be performed in a different order or performed in parallel (e.g. simultaneously).

Figure 8:
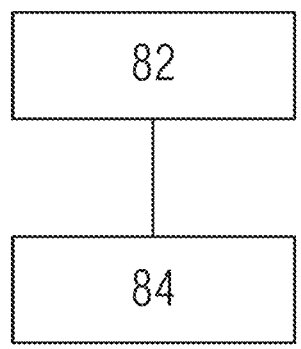
FIG. 8 is a structural schematic diagram of an apparatus for determining a respiration phase of a respiration signal, in accordance with an embodiment of the present disclosure.

An embodiment of the present disclosure further provides an apparatus for determining a respiration phase of a respiration signal. FIG. 8 is a structural schematic diagram of an apparatus for determining a respiration phase of a respiration signal according to an embodiment of the present disclosure. As shown in FIG. 8, the apparatus comprises an extraction module 82 and a determining module 84. The apparatus as shown in FIG. 8 may be integrated as part of the computing apparatus 100 shown and discussed herein with reference to FIG. 10 (e.g. the extraction module 82 and the determining module 84 may form part of the CPU 1010), function in communication with the computing apparatus 100 (e.g. via communication unit 1060), or function as a separate and independent apparatus.

The extraction module 82 is configured to extract respiration characteristic values from the respiration signal for the purpose of training an SVM model. These respiration characteristics include but are not limited to, e.g. a distance characteristic value, a score characteristic value, and an area characteristic value.

In an exemplary embodiment of the present disclosure, the distance characteristic value is calculated by the following formula:

$$f1=(t\_min1-t\_max1)/(t\_max2-t\_min1).\quad \text{Eqn. 6:}$$

f1 denotes the distance characteristic value, t_min1 denotes a trough point between two adjacent waveforms in the respiration signal, t_max1 denotes a crest point of a first waveform, and t_max2 denotes a crest point of a second waveform.

In an exemplary embodiment of the present disclosure, suppose that the time points of 80% of the amplitudes of the maximum point and minimum point are a first time t_1 and a second time t_2 respectively, i.e. the following conditions are met:

$$\mathrm{mag}(t\_1)=\mathrm{mag}(t\_max1)*0.8+\mathrm{mag}(t\_min1)*0.2 \text{ and}$$
$$\mathrm{mag}(t\_2)=\mathrm{mag}(t\_max1)*0.2+\mathrm{mag}(t\_min1)*0.8.$$

After the first time t_1 and second time t_2 have been calculated by the above equations, the formula f2=(t_max1−t_1)/(t_min1−t_2) is used to calculate the score characteristic value, and the equation f3=s(t_max1, t_max2)/s(t_min1, t_min2) is used to calculate the area characteristic value, wherein f2 denotes the score characteristic value, f3 denotes the area characteristic value, s(t1, t2) is defined as the area of a closed polygon formed between the waveform and all time points from time t1 to t2, e.g. s(t_max1, t_max2) denotes the area of the closed polygon formed by reach of the time points from time t_max1 to t_max2, and s(t_min1, t_min2) denotes the area of the closed polygon formed by each of the time points from time t_min1 to t_min2.

After these respiration characteristic values have been extracted from the respiration signal, the determining module 84 uses these respiration characteristic values to train the SVM model, i.e. a respiration signal model. When the SVM model has been trained, the model can be used to determine a respiration phase.

Figure 9:
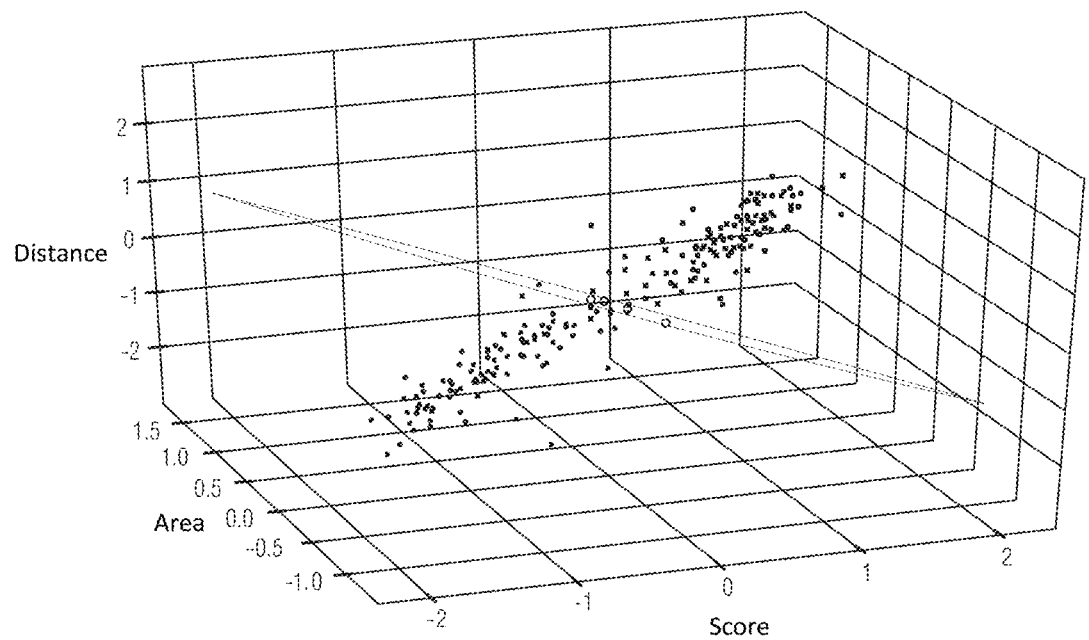
FIG. 9 is a schematic diagram of a classification result using the respiration characteristic values in accordance with an embodiment of the present disclosure.

FIG. 9 is a schematic diagram of a classification result using the respiration characteristic values of an embodiment of the present disclosure. As shown in FIG. 9, the three axes represent the distance characteristic, score characteristic, and area characteristic respectively; the solid square dots represent a crest part, in the waveform, of the EOE phase determined by classifier classification after inputting the distance characteristic value, the score characteristic value, and the area characteristic value; the solid round dots represent a trough part, in the waveform, of the EOE phase determined by classifier classification after inputting the distance characteristic value, score characteristic value, and area characteristic value. In this way, the EOE phase of the respiration signal is determined, and hence an MR system can be triggered to perform a scan in the EOE phase to improve MR image quality, avoiding motion artifacts.

A schematic embodiment of the present disclosure further provides an MRI method. The MRI method is an image outputting method. First, the method for determining a respiration phase of a respiration signal according to the present disclosure is used to determine a respiration phase. Second, magnetic resonance imaging of an examination region of an examination subject is performed according to the determined respiration phase. Specifically, an MRI system is triggered to perform a scan in the EOE phase of the respiration signal, thereby avoiding motion artifacts in the MR image, and it is thus possible to generate an image of living tissue with high precision.

A schematic embodiment of the present disclosure further provides an MRI system, comprising the apparatus for determining a respiration phase provided in the present disclosure and an imaging apparatus, which is not shown in the Figures for purposes of brevity but may operate in accordance with known MR imaging systems. For instance, after an examination subject has been placed in the MRI system, the apparatus for determining a respiration phase provided in the present disclosure is used to determine a respiration phase of a respiration signal, in particular an EOE phase. Next, the MRI system is triggered at a start time point of the EOE phase to transmit an MR signal and perform a scan, and gradient coils are used to modify an external magnetic field, i.e. a body layer of the examination subject is selected while generating MR signal region encoding. An MR signal is then reconstructed, e.g. by means of a Fourier transform, to generate an image of the selected body layer, for the purpose of medical diagnosis. MR signal generation and detection is achieved using a high-frequency system; this system comprises a transmitting antenna for sending high-frequency excitation pulses into the body of the examination subject, and a receiving antenna for receiving resonance signals modulated by the examination subject.

Figure 10:
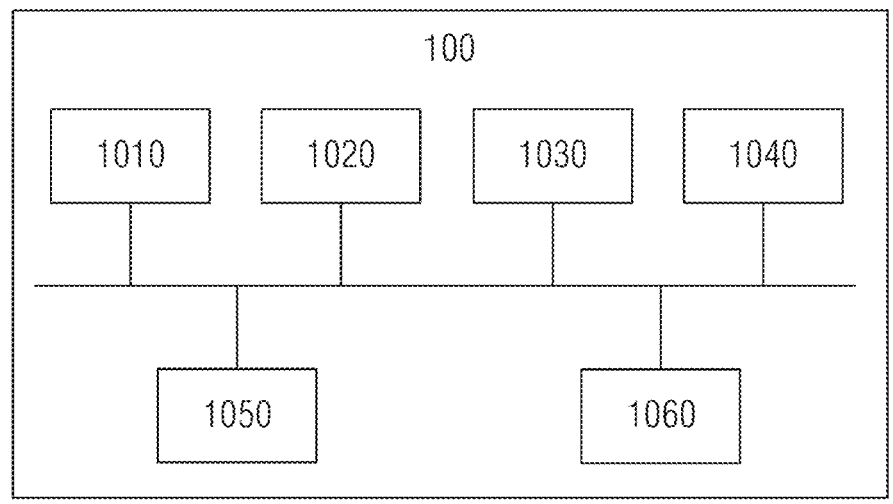
FIG. 10 is a schematic diagram of an example of a computing apparatus 100, which serves as part of a hardware part of an apparatus for implementing the method for determining a respiration phase of a respiration signal, in accordance with an embodiment of the present disclosure.

FIG. 10 is a schematic diagram of a practical example of a computing apparatus 100, which serves as part of a hardware part of an apparatus for implementing the method for determining a respiration phase of a respiration signal according to an embodiment of the present disclosure. As shown in FIG. 10, the computing apparatus 100 may comprise a CPU 1010 for performing overall control, a Read Only Memory (ROM) 1020 for storing system software, a Random Access Memory (RAM) 1030 for storing write-in/readout data, a storage unit 1040 for storing various programs and data, an input/output unit 1050 as an input/output interface, and a communication unit 1060 for realizing communication functionality. Alternatively, the CPU 1010 may be replaced by a processor such as a microprocessor MCU or programmable logic device FPGA. The input/output unit 1050 may comprise various interfaces such as an input/output interface (I/O interface), a universal serial bus (USB) port (which may be included as one of the I/O interface ports) or a network interface. Those skilled in the art will understand that the structure shown in FIG. 10 is merely schematic, and does not impose limitations on the hardware structure of a main control system. For example, the computing apparatus 100 may further comprise alternate components, or a larger or smaller number of components than that shown in FIG. 10, or may have a different configuration from that shown in FIG. 10.

It should be noted that the CPU 1010 may comprise one or more processors; the one or more processors and/or other data processing circuits can in general be referred to as "apparatuses for determining a respiration phase" in the present disclosure. The data processing circuit may be completely or partially embodied as software, hardware, firmware or any other combination. In addition, the data processing circuit may be a single independent processing module, or completely or partially incorporated in any one of the other components in the computing apparatus 100.

The storage unit 1040 may be used to store software programs and modules of application software, such as a program instruction/data storage apparatus corresponding to a main control instruction computing method described in the present disclosure; the CPU 1010 realizes the abovementioned main control instruction computing method by running the software programs and modules stored in the storage unit 1040. The storage unit 1040 may comprise a non-volatile memory, such as one or more magnetic storage apparatuses, internal memories, or other non-volatile solid-state memories. In some practical examples, the storage unit 1040 may further comprise a memory disposed remotely from the CPU 1010; these remote memories may be connected to the computing apparatus 100 via a network. Real examples of the abovementioned network include but are not limited to the internet, intranets, local area networks, mobile communication networks and combinations thereof.

Again, an embodiment of the present disclosure further provides a non-transitory readable storage medium having a program stored thereon and, when the program is executed, a processor is caused to execute the method provided in the present disclosure for determining a respiration phase of a respiration signal. The non-transitory readable storage medium may be identified with the storage unit 1040 or a different storage unit not shown in the Figures, and the processor may be identified with the CPU 1010 or a different processor not shown in the Figures. The computing apparatus 100 may form part of and/or be in communication with a magnetic resonance scanning system, such as a control computer or other computing components that may be used by a MRI scanner to perform MR imaging of an examination region of an examination subject according to the determined respiration phase. Thus, the non-transitory readable storage medium may store instructions that are executed by the CPU 1010 or other suitable components of a MRI scanner or apparatus to perform the methods as discussed herein, which include, once determined, using the determined respiration phase to perform an MR imaging of an examination region of an examination subject.

The communication unit 1060 is used for receiving or sending data via a network. Specific examples of the abovementioned network may include a wireless network provided by a communication supplier of the computing apparatus 100. In an example, the communication unit 1060 comprises a network adapter (Network Interface Controller, NIC), which may be connected to other network equipment via a base station and can communicate with the internet. In an example, the communication unit 1060 may be a Radio Frequency (RF) module used to communicate with the Internet wirelessly.

In an embodiment of the present disclosure, a respiration signal model is trained on the basis of a machine learning method such as an SVM method by extracting characteristic values of a respiration signal such as a Pilot Tone respiration signal, and a respiration phase of the respiration signal is further determined on the basis of the respiration signal model, resulting in the beneficial effects of robustness, high performance, and support for Pilot Tone applications.

Only example embodiments of the present disclosure are described above. It should be pointed out that those skilled in the art can make improvements and modifications without departing from the principle of the present disclosure, and that these improvements and modifications should also fall within the scope of protection of the present disclosure.

The various functional blocks, apparatuses, modules, units, components of physical or functional units, etc., as shown in the drawings and described herein may be implemented via any suitable number and type of computer processors, hardware components, the execution of software algorithms, or combinations thereof, and thus may alternatively be referred to as a "unit," "system," "circuitry," "processor(s)," or a "device."

What is claimed is:

1. A method for determining a respiration phase of a respiration signal, comprising:
   extracting, via one or more processors, a distance characteristic value, a score characteristic value, and an area characteristic value from the respiration signal, the distance characteristic value, the score characteristic value, and the area characteristic value indicating a waveform variation between two adjacent waveforms in the respiration signal;
   training, via one or more processors, a respiration signal model according to the distance characteristic value, the score characteristic value, and the area characteristic value;
   determining, via one or more processors, the respiration phase of the respiration signal using the respiration signal model; and
   performing, via a magnetic resonance imaging (MRI) apparatus, magnetic resonance imaging of an examination region of an examination subject using the determined respiration phase,
   wherein the area characteristic value represents a ratio of (i) an area formed by two crest points of the two adjacent waveforms in the respiration signal and a trough point between the two adjacent waveforms in the respiration signal to (ii) an area formed by a second waveform of the two adjacent waveforms in the respiration signal.

2. The method as claimed in claim 1, wherein the distance characteristic value represents a ratio of (i) a width of a second-half-waveform of a first waveform of the two adjacent waveforms in the respiration signal to (ii) a width of a first-half-waveform of a second waveform of the two adjacent waveforms in the respiration signal.

3. The method as claimed in claim 1, wherein the score characteristic value represents a ratio of (i) a width of a rising waveform portion leading to a crest point of a first waveform of the two adjacent waveforms in the respiration signal to (ii) a width of a falling waveform portion leading to a trough point of the first waveform.

4. The method as claimed in claim 1, further comprising:
prior to extracting the distance characteristic value, the score characteristic value, and the area characteristic value from the respiration signal:
acquiring the two crest points of the two adjacent waveforms in the respiration signal as a first maximum point and a second maximum point, respectively;
acquiring the trough point between the two adjacent waveforms in the respiration signal as a first minimum point;
acquiring a trough point of the second waveform after the second maximum point as a second minimum point; and
determining time points corresponding to the first maximum point, the first minimum point, the second maximum point, and the second minimum point, respectively, as a first maximum time point, a first minimum time point, a second maximum time point, and a second minimum time point.

5. The method as claimed in claim 4, wherein extracting the distance characteristic value from the respiration signal comprises:
calculating a ratio of (i) a difference value between the first minimum time point and the first maximum time point to (ii) the difference value between the second maximum time point and the first minimum time point; and
extracting the distance characteristic value as the calculated ratio.

6. The method as claimed in claim 4, wherein extracting the score characteristic value from the respiration signal comprises:
determining, based on a predetermined amplitude ratio parameter, the first maximum point, and the first minimum point, (i) a start time point of a rising waveform portion leading to the first maximum point of a first waveform of the two adjacent waveforms, and (ii) a start time point of a falling waveform portion leading to the first minimum point of the first waveform, as (i) a first time point, and (ii) a second time point, respectively, for determining an end-of-expiration start time point of the respiration phase;
calculating a ratio of (i) a difference value between the first maximum time point and the first time point to (ii) a difference value between the first minimum time point and the second time point; and
extracting the score characteristic value as the calculated ratio.

7. The method as claimed in claim 6, wherein:
the first time point is determined by evaluating:

$$mag(t\_1)=mag(t\_max1)*p+mag(t\_min1)*(1-p),$$

the second time point is determined by evaluating:

$$mag(t\_2)=mag(t\_max1)*(1-p)+mag(t\_min1)*p,$$

t_1 represents the first time point,
t_max1 represents the first maximum time point,
p represents an amplitude ratio parameter,
t_min1 represents the first minimum time point, and
mag represents an amplitude function.

8. The method as claimed in claim 7, wherein the amplitude ratio parameter p is equal to 80%.

9. The method as claimed in claim 4, wherein extracting the area characteristic value from the respiration signal comprises:
calculating a ratio of (i) a first polygon area determined by the first maximum point, the second maximum point, and the first minimum point to (ii) a second polygon area determined by the first minimum point, the second maximum point, and the second minimum point; and
extracting the area characteristic value as the calculated ratio.

10. An apparatus for determining a respiration phase of a respiration signal, comprising:
extraction circuitry configured to extract a distance characteristic value, a score characteristic value, and an area characteristic value from the respiration signal, the distance characteristic value, the score characteristic value, and the area characteristic value indicating waveform variation between two adjacent waveforms in the respiration signal; and
determining circuitry configured to (i) train a respiration signal model according to the distance characteristic value, the score characteristic value, and the area characteristic value, and (ii) determine the respiration phase of the respiration signal using the respiration signal model,
wherein a magnetic resonance imaging (MRI) apparatus uses the determined respiration phase of the respiration signal to perform magnetic resonance imaging of an examination region of an examination subject, and
wherein the area characteristic value represents a ratio of (i) an area formed by two crest points of the two adjacent waveforms in the respiration signal and a trough point between the two adjacent waveforms in the respiration signal to (ii) an area formed by a second waveform of the two adjacent waveforms in the respiration signal.

11. The apparatus as claimed in claim 10, wherein the extraction circuitry is further configured to:
acquire the two crest points of the two adjacent waveforms of the respiration signal as a first maximum point and a second maximum point, respectively;
acquire the trough point between the two adjacent waveforms of the respiration signal as a first minimum point;
acquire a trough point of the second waveform after the second maximum point as a second minimum point; and
determine time points corresponding to the first maximum point, the first minimum point, the second maximum point, and the second minimum point, respectively, as a first maximum time point, a first minimum time point, a second maximum time point, and a second minimum time point.

12. The apparatus as claimed in claim 11, wherein the extraction circuitry is further configured to:
calculate a ratio of (i) a difference value between the first minimum time point and the first maximum time point to (ii) a difference value between the second maximum time point and the first minimum time point; and
extract the distance characteristic value as the calculated ratio.

13. The apparatus as claimed in claim 11, wherein the extraction circuitry is further configured to:
determine, based on a predetermined amplitude ratio parameter, the first maximum point, and the first minimum point, (i) a start time point of a rising waveform portion leading to the first maximum point of a first waveform of the two adjacent waveforms, and (ii) a start time point of a falling waveform portion leading to the first minimum point of the first waveform, as (i) a first time point, and (ii) a second time point, respectively, to determine an end-of-expiration start time point of the respiration phase;

calculate a ratio of (i) a difference value between the first maximum time point and the first time point to (ii) a difference value between the first minimum time point and the second time point; and extract the score characteristic value as the calculated ratio.

14. The apparatus as claimed in claim 11, wherein the extraction circuitry is further configured to:

calculate a ratio of (i) a first polygon area determined by the first maximum point, the second maximum point, and the first minimum point to (ii) a second polygon area determined by the first minimum point, the second maximum point, and the second minimum point; and extract the area characteristic value as the calculated ratio.

15. A non-transitory readable storage medium having a program stored thereon that, when executed by one or more processors, cause the one or more processors to:

extract a distance characteristic value, a score characteristic value, and an area characteristic value from a respiration signal, the distance characteristic value, the score characteristic value, and the area characteristic value indicating a waveform variation between two adjacent waveforms in the respiration signal;

train a respiration signal model according to the distance characteristic value, the score characteristic value, and the area characteristic value;

determine a respiration phase of the respiration signal using the respiration signal model; and perform a magnetic resonance imaging of an examination region of an examination subject using the determined respiration phase, wherein the area characteristic value represents a ratio of (i) an area formed by two crest points of the two adjacent waveforms in the respiration signal and a trough point between the two adjacent waveforms in the respiration signal to (ii) an area formed by a second waveform of the two adjacent waveforms in the respiration signal.

16. The method as claimed in claim 1, wherein the determined respiration phase is a phase within a respiratory motion cycle of the examination subject that comprises an expiration phase, an aspiration phase, and an end-of-expiration (EOE) phase.

17. The method of claim 16, further comprising:

triggering the MRI apparatus to perform the magnetic resonance imaging of the examination region of the examination subject at a start time point of the EOE phase of the respiratory motion cycle of the examination subject.

18. The method as claimed in claim 1, wherein the area formed by the second waveform comprises an area formed by three points in the second waveform.

19. The method as claimed in claim 1, wherein:

the ara formed by the two crest points of the two adjacent waveforms in the respiration signal and the trough point between the two adjacent waveforms in the respiration signal comprises a first polygon area, the area formed by the second waveform of the two adjacent waveforms in the respiration signal comprises a second polygon area, and extracting the area characteristic value comprises calculating a ratio of the first polygon area to the second polygon area.

* * * * *